US005651769A

United States Patent [19]
Waxman et al.

[11] Patent Number: 5,651,769
[45] Date of Patent: Jul. 29, 1997

[54] METHOD FOR RETRIEVING PANCREATIC JUICE UTILIZING AND ENDOSCOPICALLY WIRE-GUIDED CATHETER

[75] Inventors: Irving Waxman, Newton; Steven Freedman, Brighton, both of Mass.

[73] Assignee: The Beth Israel Hospital Association, Boston, Mass.

[21] Appl. No.: 543,612

[22] Filed: Oct. 16, 1995

[51] Int. Cl.$^6$ .................................................. A61M 31/00
[52] U.S. Cl. ............................................ 604/54; 128/760
[58] Field of Search ........................... 604/280, 51, 54, 604/96, 101; 128/753, 754; 606/167, 170; 600/104

[56] References Cited

U.S. PATENT DOCUMENTS

| | | | |
|---|---|---|---|
| 4,905,667 | 3/1990 | Foerster et al. | 600/104 |
| 4,949,706 | 8/1990 | Thon | 600/104 |
| 5,334,143 | 8/1994 | Carroll | 604/54 |
| 5,379,779 | 1/1995 | Rowland et al. | 128/772 |

OTHER PUBLICATIONS

"Chronic Pancreatitis" authored by Michael L. Steer, M.D., Irving Waxman, M.D., and Steven Freedman, M.D., dated Jun. 1, 1995 from the *New England Journal of Medicine*.

*Primary Examiner*—Sam Rimell
*Assistant Examiner*—Pamela Y. Wingood
*Attorney, Agent, or Firm*—Lorusso & Loud

[57] ABSTRACT

A method for accurately and quickly positioning a double lumen gastroduodenal tube into predetermined locations utilizing an endoscopically placed guide wire to retrieve duodenal fluid uncontaminated by gastric fluid, with little or no discomfort to the patient, and minimal radiation exposure. Specifically, an endoscope is passed through a patent's esophagus and stomach into the duodenum such that its distal end is located at a predetermined location, such as the fourth portion of the duodenum. While the endoscope is held in place, a guide-wire is passed through its center instrument channel to position a distal end of the guide-wire adjacent to the distal end of the endoscope. The endoscope is then withdrawn from the patient, leaving the guide-wire. A double lumen gastroduodenal tube is then threaded over the guide-wire such that gastric ports are aligned with the stomach and duodenal ports are aligned with the fourth portion of the duodenum so that upon aspiration of the gastric ports, the gastric fluid is prevented from entering the duodenum and contaminating the duodenal fluid.

20 Claims, 6 Drawing Sheets

METHOD FOR RETRIEVING PANCREATIC JUICE UTILIZING AND ENDOSCOPICALLY WIRE-GUIDED CATHETER

FIELD OF THE INVENTION

The present invention relates generally to a method for using a catheter to diagnose chronic pancreatitis and, more specifically, to a method for positioning a double lumen gastroduodenal robe using an endoscopically-placed guide-wire.

BACKGROUND OF THE INVENTION

Chronic pancreatitis is usually characterized by a progressive loss of pancreatic parenchymal tissue. In many individuals, chronic pancreatitis is clinically silent. Further, many patients with unexplained abdominal pain may actually have chronic pancreatitis that eludes diagnosis. Chronic pancreatitis is associated with a mortality rate that approaches 50 percent within 20 to 25 years. Approximately 15 to 20 percent of patients die of complications associated with attacks of pancreatitis. It has recently been reported that pancreatic cancer develops in approximately 4 percent of patients within 20 years of a diagnosis of chronic pancreatitis.

With the rapid evolution of pancreatic imaging over the last two decades, computerized tomography and endoscopic retrograde pancreatography (ERP) have become invaluable tools in the evaluation and management of pancreatic disorders. Nevertheless, chronic pancreatitis has been reported in up to 24% of patients having a negative diagnosis with these non-invasive techniques.

Direct invasive pancreatic function testing plays an important role in the diagnosis of abdominal pain of unclear etiology, especially when pancreatic disease is suspected in spite of negative imaging tests. Conventional invasive techniques for pancreatic juice collection used to supplement or replace the above imaging techniques include the secretin-pancreozymin test as well as the intraductal sampling technique.

The secretin-pancreozymin test involves the collection of duodenal fluid and the measurement of various characteristics after the inducement of pancreatic functions. Although the secretin-pancreozymin test has been shown to have a sensitivity and specificity in the 90% range, its use in the United States has been limited to few specialized centers. This is due to its complexity and cumbersome nature, resulting in the inability to successfully pass a Dreiling™ catheter into the duodenum of approximately 20–50% of the patients. This degree of difficulty increases the cost of the procedure by requiring the administration by trained technicians. Furthermore, the time involved to pass the catheter into the duodenum on the remaining 50–80% of the patients takes from 0.5 to 2 hours. In addition, the discomfort experienced by the patient narrows the applicable use of the technique to only those extreme conditions where its use is essential. This is particularly true in patients having motility disorders of the gastrointestinal (GI) tract, which is seen in up to 20% of those referred for testing.

In the intraductal sampling technique, pure pancreatic juice is collected using a 1.5 mm catheter placed into the pancreatic duct by gastroenterologic procedures (ERP). Although this technique has been shown to yield similar results to the secretin-pancreozymin test, it requires a highly skilled endoscopist because it requires the selective localization of the main pancreatic duct, followed by deep cannulation and placement of a collection catheter deep within the pancreatic duct. Furthermore, this process has the risks inherent to an ERP.

Thus, it has been determined that chronic pancreatitis can be difficult to diagnose, especially in the initial three to five years of disease. As a result, most patients undergo repeated testing which usually includes multiple imaging and invasive evaluations.

What is needed, therefore, is a method for obtaining pancreatic juice that does not require an experienced technician to administer, and which can be successfully administered quickly and cost effectively, regardless of GI motility. Furthermore, the method must not cause significant patient discomfort to reduce patient resistance to the technique.

SUMMARY OF THE INVENTION

The present invention is an improved method for accurately and quickly positioning a double lumen gastroduodenal tube into predetermined locations utilizing an endoscopically placed guide wire to retrieve duodenal fluid uncontaminated by gastric fluid, with little or no discomfort to the patient.

Specifically, the endoscopic guide-wire placement method of the present invention includes a series of steps, the first of which is the feeding of an endoscope through the patient's esophagus and stomach into the duodenum. The endoscope is positioned such that its distal end is located at a predetermined location in the duodenum. The endoscope is then held in place while a guide-wire is passed through a center instrument channel of the endoscope to position a distal end of the guide-wire adjacent to the distal end of the endoscope. Once it is verified that the guide-wire is properly placed, the endoscope is withdrawn from the patient, leaving the guide-wire. The position of the guide-wire is then verified by fluoroscopy.

A double lumen gastroduodenal tube is then threaded over the guide-wire. The tube includes a duodenal lumen disposed adjacent to a separate gastric lumen for removing duodenal and gastric fluids, respectively. In an alternative embodiment, the duodenal lumen is concentrically disposed within the separate gastric lumen. The gastric lumen has gastric ports at its distal end for receiving gastric fluid. Similarly, duodenal ports are placed at a distal end of the duodenal lumen, which extends beyond the gastric lumen, for receiving duodenal fluid.

Proper placement of the tube is achieved when the gastric ports are aligned with the stomach and the duodenal ports are aligned with a predetermined portion of the duodenum. This placement may be verified by fluoroscopy. Once the proper location of the ports is verified, the guide-wire is withdrawn from the patient.

To retrieve uncontaminated duodenal fluids, the gastric fluids are continuously aspirated through the gastric ports to prevent the gastric fluids from entering the duodenum. Simultaneously, the duodenal fluid is aspirated through the duodenum ports for subsequent analysis of the duodenal fluid.

Alternatively, other methods are contemplated for preventing gastric fluid contamination of the duodenal fluid prior to aspiration. For example, a balloon may be incorporated into the procedure in place of the gastric tureen. Specifically, an endoscopic wire-guided method similar to that described above is implemented to place a duodenal tube in a desired location of the duodenum. Then, a tube having a balloon at its distal end may be placed over the a duodenal tube to position the balloon at a location between the stomach and an entry point at which the pancreatic juice enter said duodenum. The balloon is then inflated to prevent gastric fluids from entering the duodenum. While the balloon is inflated the duodenal fluid is aspirated as above.

Advantageously, the present invention enables the accurate placement of the double lumen gastroduodenal tube within minutes, thereby reducing discomfort and adverse reactions by the patient. In addition, the present invention can be successfully completed on all patients. Furthermore, implementation of this process may be performed by technicians in an GI endoscopy unit without the need for specialized trained personnel.

Moreover, the use of an endoscopically placed guide wire eliminates the need to gravity feed the catheter by following an unobstructed path. Significantly, the present invention enables rapid tube placement regardless of gastrointestinal motility. Furthermore, the rapid tube placement reduces the time in which fluoroscopy is utilized. As a result of the decreased fluoroscopy, the patient and technicians are exposed to significantly decreased radiation level. In some instances, for example, a reduction in radiation exposure of up to 75% has been achieved.

Further features and advantages of the present invention as well as the structure and operation of various embodiments of the present invention are described in detail below with reference to the accompanying drawings. The principles and features of this invention may be employed in various and numerous embodiments without departing from the scope of the invention. In the drawings, like reference numbers indicate identical or functionally similar elements. Additionally, the left-most digit of a reference number identifies the drawing in which the reference number first appears.

BRIEF DESCRIPTION OF THE DRAWINGS

For a fuller understanding of the nature of the invention, reference should be had to the following detailed description taken in connection with the accompanying drawings, in which.

DETAILED DESCRIPTION OF THE PREFERRED EMBODIMENTS

The present invention is an improved method for accurately and quickly positioning a double lumen gastroduodenal robe into predetermined locations utilizing an endoscopically placed guide wire to retrieve duodenal fluid uncontaminated by gastric fluid, with little or no discomfort to the patient.

Figure 1:
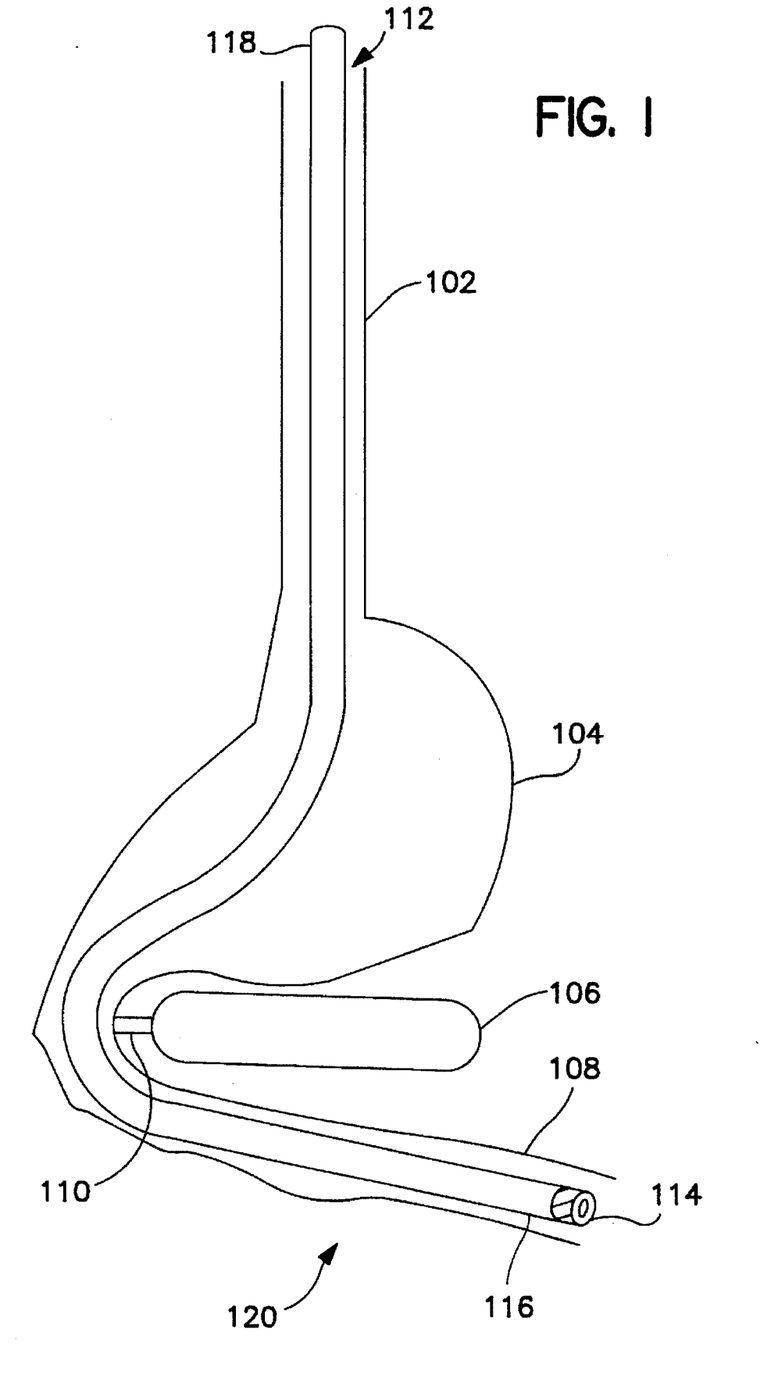
FIG. 1 is an illustration of a first step of the preferred embodiment of the present invention wherein an endoscope is positioned through a patient's esophagus, stomach and duodenum.

FIGS. 1–5 illustrate the location of the endoscope, guide-wire, and double lumen catheter after each of the steps of the preferred embodiment of the present invention. Referring to FIG. 1, the endoscopic guide-wire placement method of the present invention includes a first step which is the feeding of an endoscope 112 through the patent's esophagus 102 and stomach 104 into the duodenum 108.

Endoscope 112 has a proximate end 118 that does not enter the patient's body and a distal end 116 having a camera 114. Specifically, the endoscope 112 is positioned such that its distal end 116 is located at a predetermined location in duodenum 108 wherein at a later step duodenal fluid is aspirated. (discussed below). Generally, the duodenal fluid is aspirated distal to the ampulla of vater. The ampulla of vater is the structure in which the pancreatic duct 110, which extends from the pancreas 106, enters the duodenum 108. In the preferred embodiment the predetermined location is the fourth portion 120 of duodenum 108. This step is completed once endoscope 112 is properly positioned in the duodenum 108. This may be verified, for example, by fluoroscopy.

In the preferred embodiment of the present invention, the endoscope is a commonly available standard 9 mm videoendoscope. However, other types endoscopes may be used that are appropriate for a given application.

Figure 2:
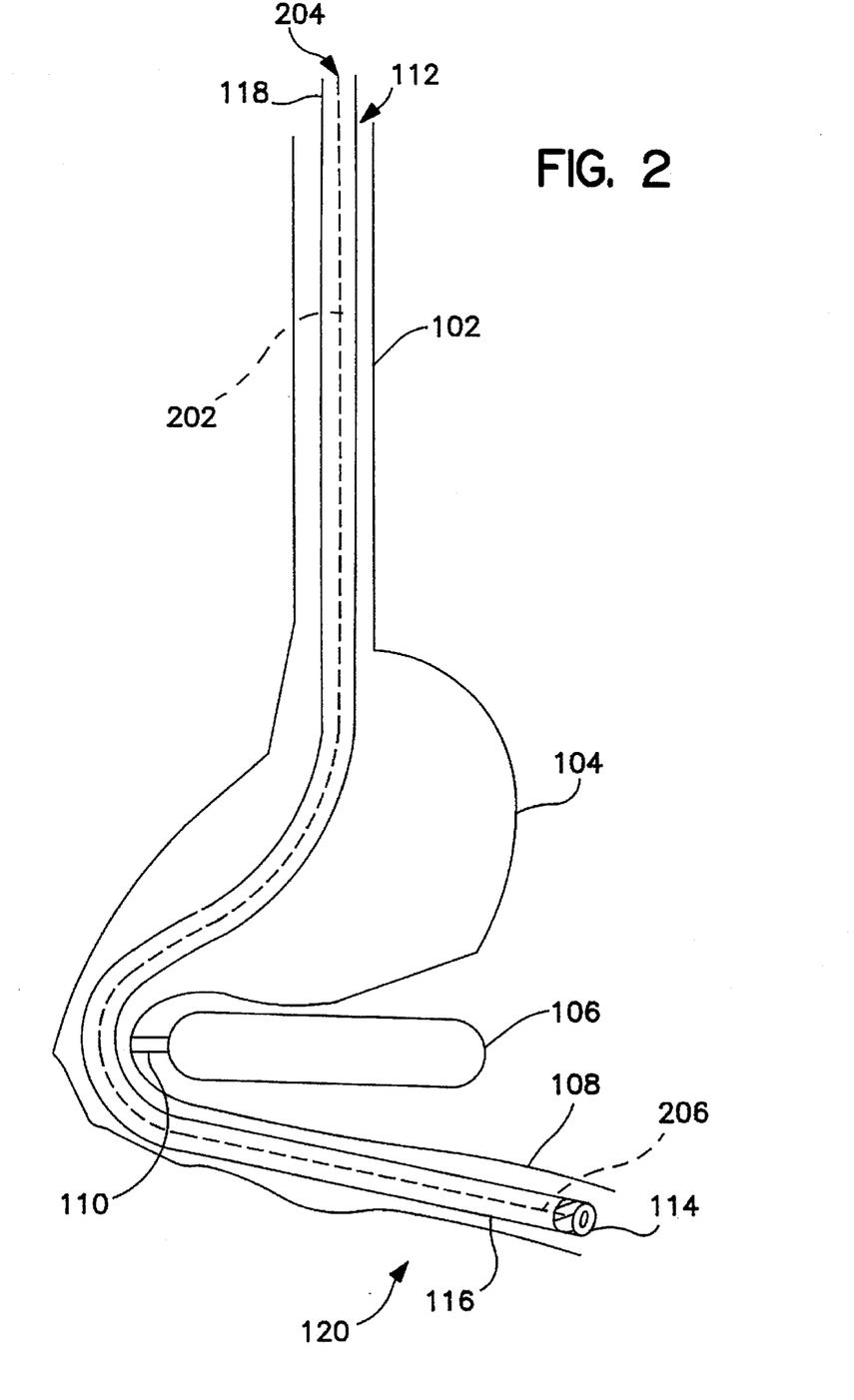
FIG. 2 is an illustration of a subsequent step of the present invention wherein a guide-wire is passed through a center channel of the endoscope.

FIG. 2 is an illustration of the next step of the present invention wherein a guide-wire 202 (shown by dashed lines) is passed through a center instrument channel 204 of endoscope 112. The diameter of the center instrument channel of endoscope 112 is dimensioned, with respect to the guide-wire, to provide sufficient wire clearance to allow the guide-wire to be moved easily through the endoscope in an axial direction, during placement of the guide-wire 202.

Under fluoroscopic guidance, all loops (not shown) of endoscope 112 are reduced and guide wire 202 (shown by dashed lines) is advanced through the endoscope center instrument channel 204 until a distal end 206 of the guide wire 202 is positioned at the predetermined location; that is, adjacent to the distal end 116 of endoscope 112 at the Ligament of Treitz 120.

In the preferred embodiment of the present invention, the guide wire is a conventional 210 cm spring tip type guide wire, available from Bard Interventional Products, Tewksbury, Mass., USA. However, as one skilled in the art would find apparent, other guide-wire types and sizes may be used that are compatible with the chosen double lumen catheter and endoscope, as well as the selected external body access site and resulting path by which the predetermined location is reached.

Figure 3:
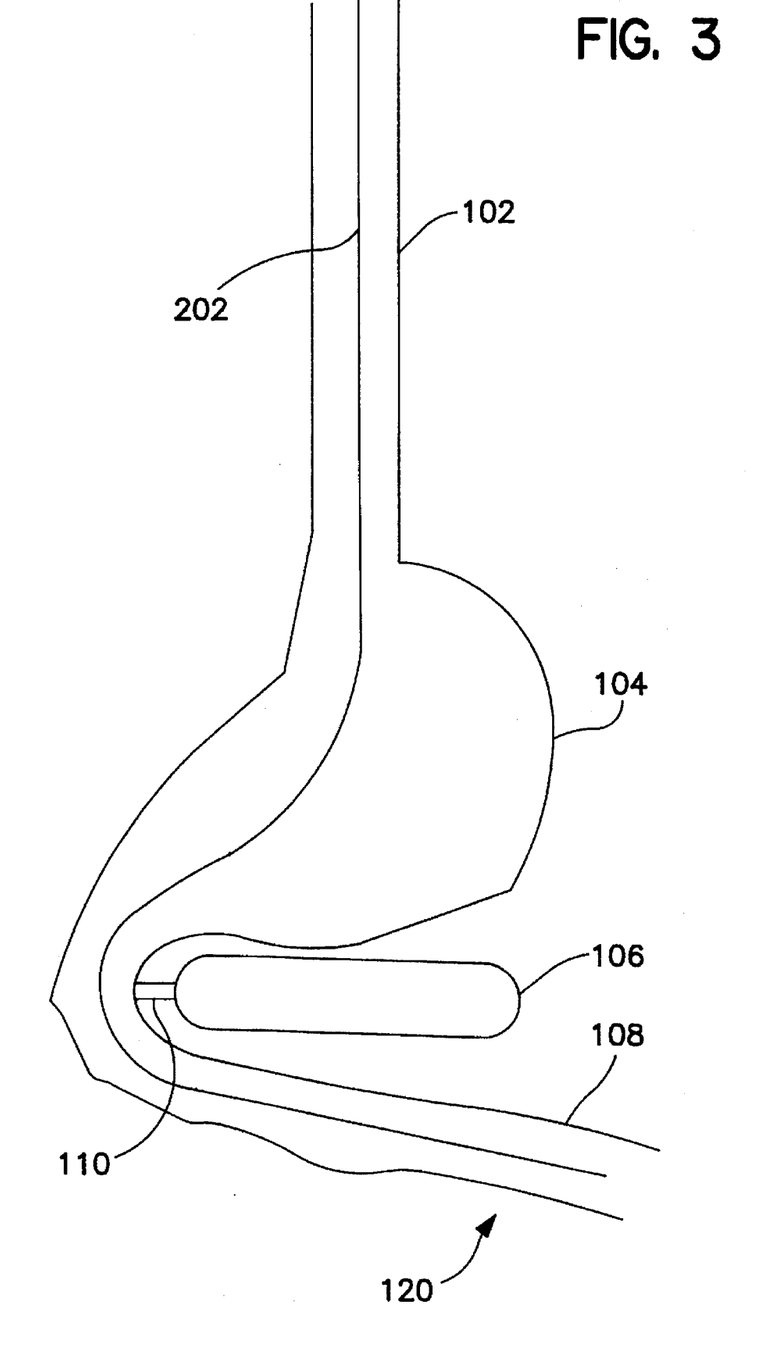
FIG. 3 is an illustration of a subsequent step of the present invention wherein the endoscope has been withdrawn from the patient, leaving the guide-wire in place.

Once it is verified that guide-wire 202 is properly placed, endoscope 112 is withdrawn from the patient, leaving the guide-wire, as shown in FIG. 3. The verification of the position of the guide wire may be performed, for example, by fluoroscopy, although other methods may be used. The use of an endoscopically placed guide wire eliminates the need to gravity feed the catheter by following an unobstructed path. Significantly, this aspect of the present invention enables rapid tube placement regardless of gastrointestinal motility (discussed below).

Figure 4:
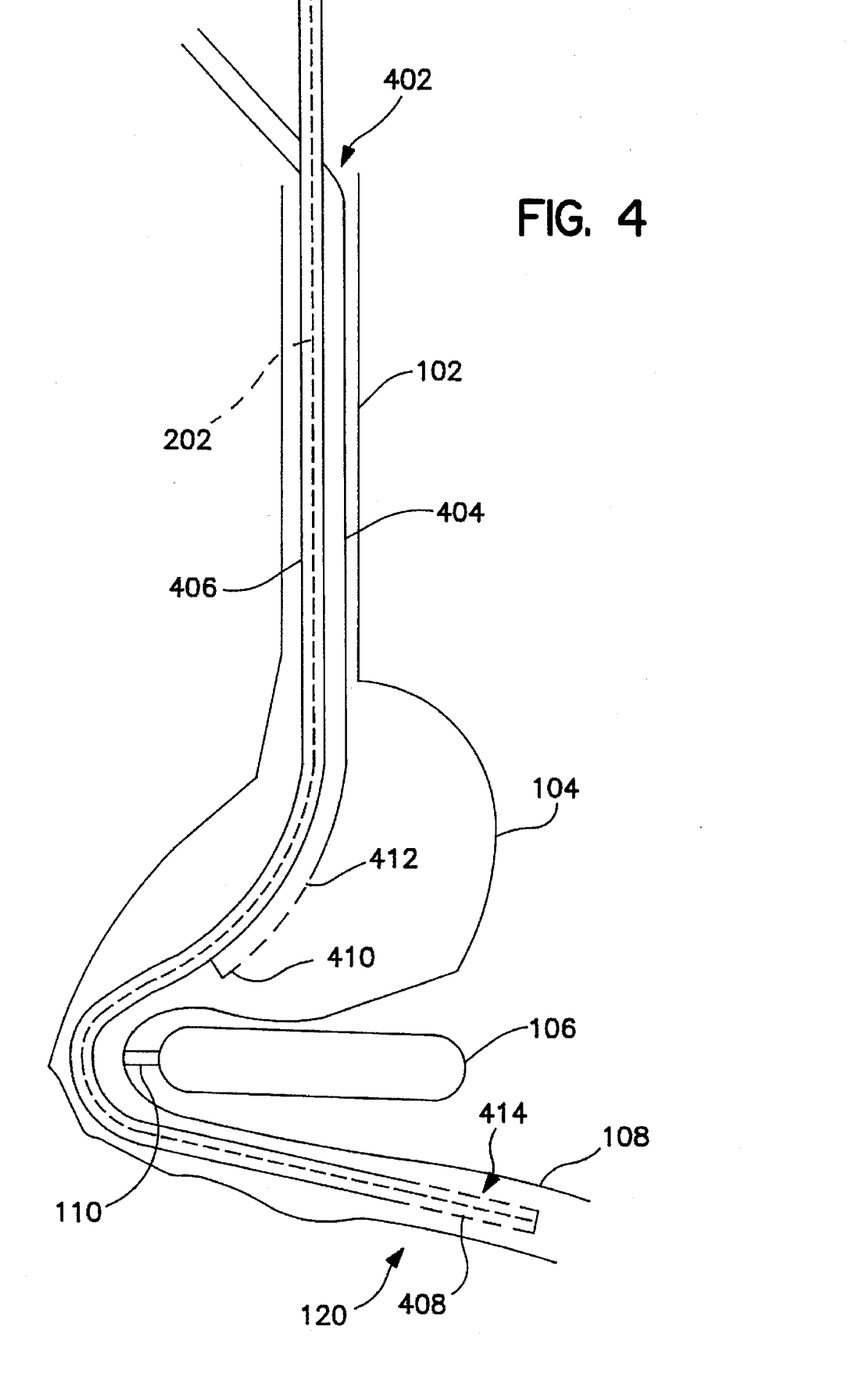
FIG. 4 is an illustration of a subsequent step of the present invention wherein a double lumen catheter is passed over the guide-wire.

Referring to FIG. 4, a double lumen gastroduodenal tube 402 is then passed over guide-wire 202 (shown by dashed lines). The guide-wire 202 is sufficiently rigid to enable the tube 402 to easily track the wire down to the predetermined location. Tube 402 includes a duodenal lumen disposed adjacent to a separate gastric lumen for removing duodenal and gastric fluids, respectively. In an alternative embodiment, the duodenal lumen is concentrically disposed within the separate gastric lumen. As shown in FIG. 4, the duodenal lumen 406 extends past the distal end 410 of the gastric lumen 404, which terminates at the location of the stomach 104. Gastric lumen 404 has gastric aspiration ports 412 at its distal end 410 for receiving gastric fluid. Similarly, duodenal lumen 406 has duodenal aspiration ports 414 at its distal end 408 for receiving duodenal fluid. The separate lumens 404, 406 prevent contamination of the duodenal fluid by the gastric fluid.

Since the guide wire 202 is positioned at the desired location of the duodenum, the duodenal lumen 406 is threaded over guide-wire 202, as shown in FIG. 4. While the duodenal lumen 406 is threaded over guide wire 202, tension is kept on the wire 202 to avoid looping of the tube in the stomach. (not shown) Preferably, the portion of the guide wire 202 disposed outside of the patient's body is lubricated to facilitate the threading of the tube. The inner diameter of the duodenal lumen 406 is dimensioned, with respect to the guide-wire, to provide sufficient wire clearance to allow the catheter to be moved easily over the wire in the axial direction during catheter placement and, as discussed below, guide-wire removal.

As shown in FIG. 4, the tube is advanced into the fourth portion of the duodenum 120 and its position is confirmed, preferably under fluoroscopy. At this position, gastric aspiration ports 412 are directly aligned with the stomach 104 and the duodenal aspiration ports 414 are directly aligned with duodenum 108.

In the preferred embodiment of the present invention, the double lumen gastroduodenal tube is a Dreiling™ tube, available from Davol, Inc., Cranston, R.I., USA. However, as one skilled in the art would find apparent, other types of double lumen tubes that separately aspirate gastric and duodenal fluids may be used.

Figure 5:
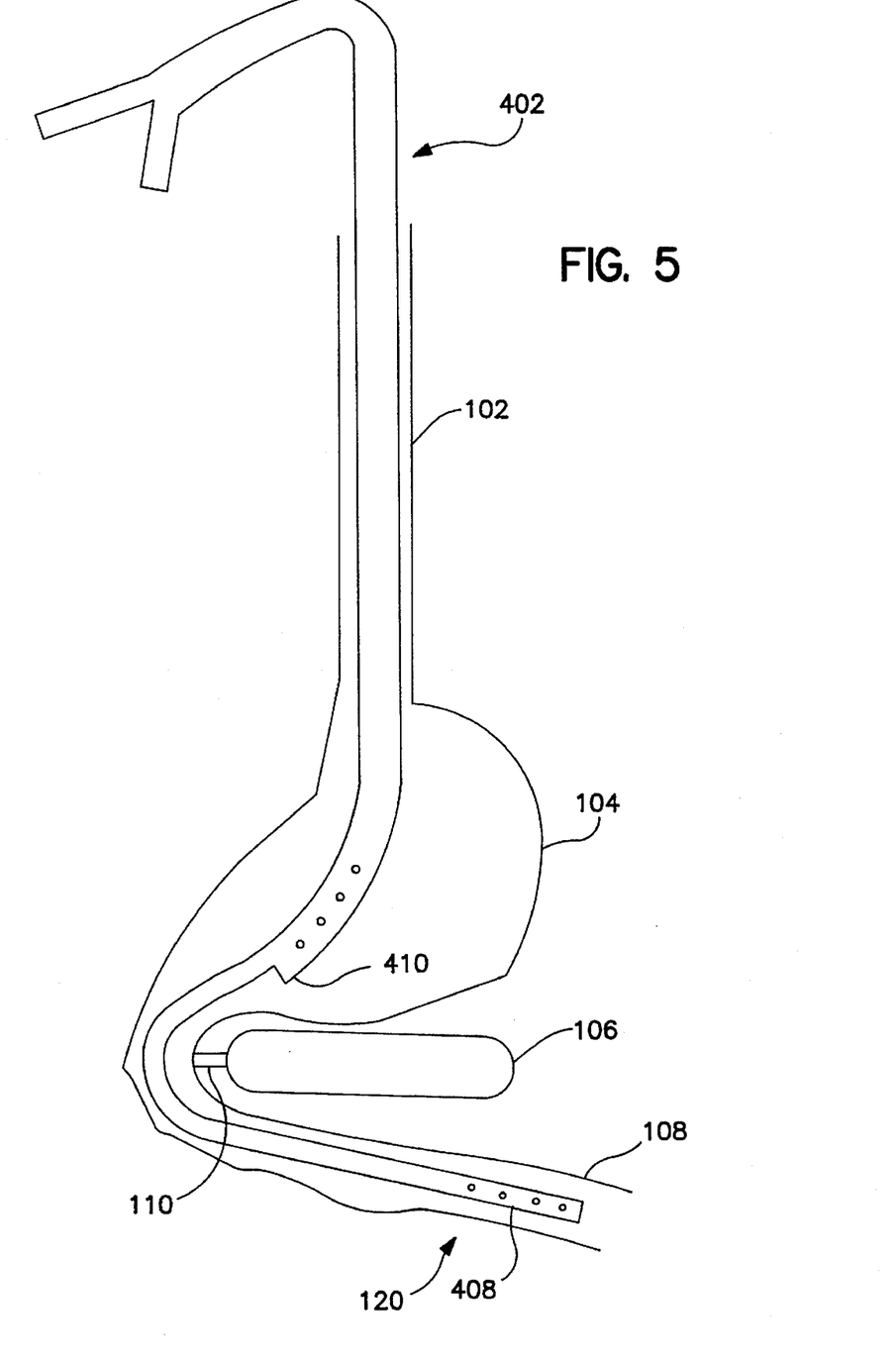
FIG. 5 is an illustration of a subsequent step of the present invention wherein the guide-wire has been withdrawn from the patient, leaving the double lumen catheter in place.

Once the proper locations of the ports 412, 414 are verified, the guide-wire 202 is withdrawn from the patient and the tube 402 is secured in its desired location as shown in FIG. 5. Advantageously, the present invention enables the accurate placement of the double tureen gastroduodenal tube 402 within minutes, thereby reducing discomfort and adverse reactions by the patient. Furthermore, implementation of this process may be performed by technicians in an GI endoscopy unit without the need for specialized trained personnel.

Significantly, the above procedures of the present invention are performed on the patient while the patient is asleep. Preferably, the patient receives topical cetacaine and is premedicated with midazolam. An intravenous line is placed in the patient and the patient is sedated with I.V. Versed in conjunction with oropharyngeal anesthesia using 10% Lidocaine spray. Subsequent to the above procures, the patient is then brought to the recovery room, and with the patient in a reclining chair the remaining procedures are performed. Since the remaining procedures are passive in nature, the patient need not remain asleep during their completion.

Figure 6:
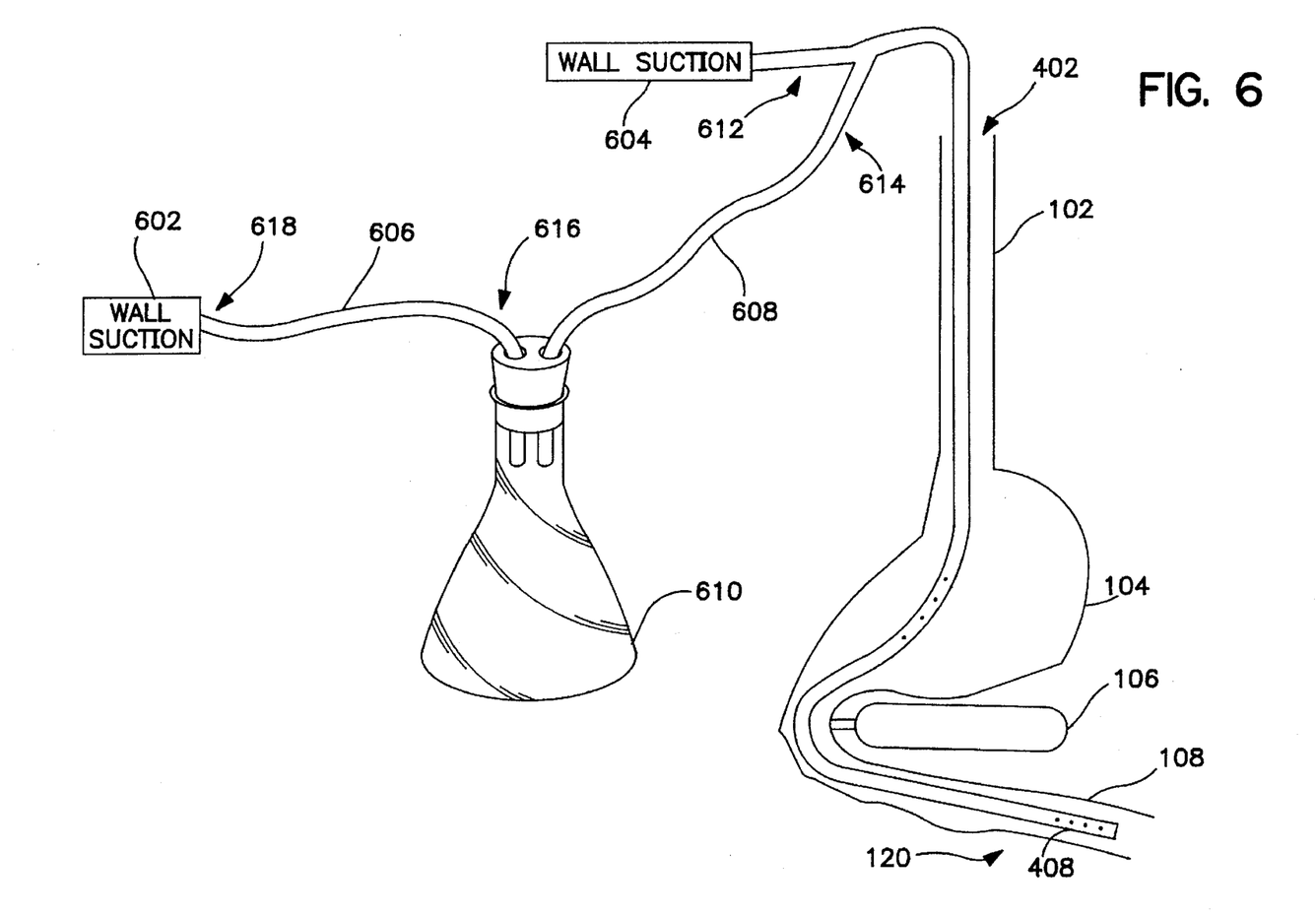
FIG. 6 is an illustration of each lumen of the double lumen catheter coupled to an aspiration device.

Referring to FIG. 6, the proximate end 614 of the duodenal lumen 406 is connected to a tube 608 which is connected to a flask 610. A first end 616 of an additional tube 606 is placed in the flask 610 with the proximate end 614 of the duodenal lumen 406. The other end 618 of the tube 606 is connected to a suction device 602. In addition, the proximate end 612 of the gastric lumen 404 is connected directly to a second suction device 604.

The suction devices 602, 604 are then activated to aspirate from the proximal ends 612, 614 of the gastric and duodenal lumen 404, 406, the gastric and duodenal fluids. To retrieve uncontaminated duodenal fluids, the gastric fluids are continuously aspirated through the gastric aspiration ports 412 from the stomach 104 to prevent the gastric fluids from entering the duodenum and mixing with the pancreatic juice entering the duodenum 108 through duct 110.

Simultaneously, the duodenal fluid is aspirated through the duodenum aspiration ports 414 from the duodenum 108 for subsequent analysis. Preferably, for chronic pancreatitis, the duodenal fluid is periodically aspirated for analysis of differential changes in the duodenal fluid.

In an alternative embodiment, the gastric fluids are prevented from contaminating the duodenal fluid prior to aspiration by the use of a balloon (not shown). The balloon may be incorporated into the procedure in place of the gastric lumen. Specifically, an endoscopic wire-guided method similar to that described above is implemented to place a single lumen tube in a desired location of the duodenum. A tube having a balloon at its distal end then may be placed over the single lumen tube to position the balloon at a location between the stomach and an entry point at which the pancreatic juice enter the duodenum through duct 110.

The balloon is then inflated to prevent gastric fluids from entering the duodenum. The guide-wire is then removed from the patient. While the balloon is inflated the duodenal fluid is periodically aspirated, as indicated above.

In another alternative embodiment, acid production by the stomach may be blocked by medication. Duodenal fluid is then periodically aspirated, as indicated above.

With respect to any of the methods identified above, once the uncontaminated duodenal fluid has been aspirated from the duodenal ports, any desired analysis, now or later developed, may be performed on the duodenal fluid to diagnose chronic pancreatitis. Specifically, in the preferred embodiment, the pH of both the gastric fluid and duodenal fluid content is calculated. The pH of the duodenal fluid is analyzed with pH paper and should be approximately 8. Fluid from the gastric port should be less than 7. Subsequent to the calculation of the pH of both fluids, the periodic aspiration of the duodenal fluid includes collecting and saving 1 to 5 ml of duodenal fluid for a baseline measurement. A secretin stimulation test is performed using the standard protocol. Specifically, secretin (1 unit/kg) is given intravenously over 1 minute via a rapid running IV line. Duodenal fluid is then collected every 15 minutes for a total of one hour. The Dreiling™ catheter is then removed. The volume of duodenal fluid collected at each 15 minute interval is recorded and an analysis is performed for total bicarbonate. Bicarbonate concentration is determined by back titration. A bicarbonate concentration of 80–120 millequivalents/liter (mEq/L) is normal. Bicarbonate concentration less than 80 mEq/L is diagnostic of chronic pancreatitis. A normal bicarbonate concentration but decreased volume output is consistent with pancreatic duct obstruction and should prompt an ERCP.

Furthermore, the terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method for positioning a double lumen gastroduodenal tube into a patient to diagnose chronic pancreatitis, comprising the steps of:

(a) passing a distal end of an endoscope from an external body access site to a predetermined location of an duodenum;

(b) passing a guide-wire through said endoscope to position a distal end of said guide-wire proximate to said distal end of said endoscope;

(c) withdrawing said endoscope from the patient;

(d) passing a double lumen gastroduodenal tube over said guide-wire to position a distal end of said tube proximate to said distal end of said guide-wire such that ports of a first lumen are located in stomach and ports of a second lumen in said predetermined location of said duodenum; and (e) withdrawing said guide-wire from the patient.

2. The method of claim 1, further comprising the step of:

(f) before said step (a), sedating the patient.

3. The method of claim 1, wherein said predetermined location is a fourth portion of said duodenum.

4. The method of claim 1, wherein said predetermined location is distal to the ampulla of vater.

5. The method of claim 1, wherein said step (b) is performed under fluoroscopic guidance.

6. The method of claim 1, wherein said step (c) includes the step of:

1) confirming said distal end of said guide-wire is proximate to said distal end of said endoscope.

7. The method of claim 6, wherein said step (c) (1) is performed with fluoroscopy.

8. The method of claim 1, further comprising the step of:

(f) lubricating said guide-wire after said step (c).

9. The method of claim 1, further comprising the step of:

(f) after said step (d) and before said step (e), verifying said position of said double lumen gastroduodenal tube such that said distal end of said second lumen is in said predetermined location of said duodenum.

10. The method of claim 9, further comprising the steps of:

(g) securing said tube after said step (e).

11. A method for obtaining duodenal fluid for use in diagnosing chronic pancreatitis of a patient, comprising the steps of:

(a) passing a distal end of an endoscope through the patient's esophagus and stomach to a predetermined location of an duodenum;

(b) passing a guide-wire through said endoscope to position a distal end of said guide-wire proximate to said distal end of said endoscope;

(c) withdrawing said endoscope from the patient;

(d) passing a double lumen gastroduodenal tube over said guide-wire to position a distal end of said tube proximate to said distal end of said guide-wire such that gastric ports of a first lumen are positioned in stomach and duodenal ports of a second lumen are positioned in said predetermined location of said duodenum;

(e) withdrawing said guide-wire from the patient;

(f) continuously aspirating gastric fluid from said gastric ports; and (g) periodically aspirating duodenal fluid from said duodenal ports.

12. The method of claim 11, further comprising the step of:

(h) performing a secretin stimulation test during said step (g).

13. The method of claim 11, further comprising the step of:

(f) before said step (a), sedating the patient.

14. The method of claim 11, wherein said predetermined location is the ampulla of vater.

15. The method of claim 11, wherein said step (c) includes the step of:

1) confirming said distal end of said guide-wire is proximate to said distal end of said endoscope.

16. The method of claim 11, further comprising the step of:

(f) after said step (d) and before said step (e), verifying said position of said double lumen gastroduodenal tube such that said distal end of said second lumen is in said predetermined location of said duodenum.

17. A method for obtaining duodenal fluid for use in diagnosing chronic pancreatitis of a patient, comprising the steps of:

(a) passing a distal end of an endoscope through the patient's esophagus and stomach to a predetermined location of an duodenum; (b) passing a guide-wire through said endoscope to position a distal end of said guide-wire proximate to said distal end of said endoscope;

(c) withdrawing said endoscope from the patient;

(d) passing a gastroduodenal tube over said guide-wire to position a distal end of said tube proximate to said distal end of said guide-wire such that duodenal ports of said tube are positioned in said predetermined location of said duodenum;

(e) passing a tube having a balloon at its distal end over said gastroduodenal tube to position said balloon at a location between said stomach and an entry point at which the pancreatic juice enter said duodenum;

(f) inflating said balloon to prevent gastric fluids from entering said predetermined location of said duodenum;

(g) withdrawing said guide-wire from the patient; and (h) periodically aspirating duodenal fluid from said duodenal ports.

18. The method of claim 17, further comprising the step of:

(f) before said step (a), sedating the patient.

19. The method of claim 17, wherein said predetermined location is the ampulla of vater.

20. The method of claim 17, further comprising the step of (f) performing each of said steps (a) through (e) under fluoroscopic guidance.

* * * * *